(12) United States Patent
Boschat et al.

(10) Patent No.: US 6,232,488 B1
(45) Date of Patent: May 15, 2001

(54) METHOD FOR HYDROGENATING DINITRILES

(75) Inventors: Vincent Boschat, Lyons; Philippe Leconte, Meyzieu; Daniel Rochette, Saint-Maurice l'Exil; Lionel Sever, Luzinay, all of (FR)

(73) Assignee: Rhodia Fiber and Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/554,887
(22) PCT Filed: Nov. 19, 1998
(86) PCT No.: PCT/FR98/02479
  § 371 Date: Sep. 19, 2000
  § 102(e) Date: Sep. 19, 2000
(87) PCT Pub. No.: WO99/26917
  PCT Pub. Date: Jun. 3, 1999

(30) Foreign Application Priority Data
Nov. 20, 1997 (FR) .................................................. 97 14809

(51) Int. Cl.$^7$ .................................................. C07C 59/74
(52) U.S. Cl. ............................................................. 558/459
(58) Field of Search ............................................. 558/459

(56) References Cited

U.S. PATENT DOCUMENTS

| 5,151,543 | 9/1992 | Ziemecki . |
| 5,508,465 | 4/1996 | Schnurr et al. . |
| 5,675,045 | 10/1997 | Bueschken et al. . |

FOREIGN PATENT DOCUMENTS

| 0 070 797 | 1/1983 | (EP) . |
| 92 12073 | 6/1993 | (WO) . |
| 93 16034 | 8/1993 | (WO) . |
| 96 18603 | 6/1996 | (WO) . |
| 98 11060 | 3/1998 | (WO) . |

*Primary Examiner*—Joseph K. McKane
*Assistant Examiner*—Joseph Murray
(74) *Attorney, Agent, or Firm*—Burns, Doane, Swecker & Mathis, L.L.P.

(57) ABSTRACT

The present invention relates to a process for the hydrogenation of aliphatic dinitriles at least partly into corresponding aminonitriles. More specifically, the invention consists of a continuous process for the hydrogenation of dinitrile, at least partly into corresponding aminonitrile, in the presence of a hydrogenation catalyst which is not dissolved in the reaction medium, characterized in that it is carried out in apparatus comprising means for the continuous separation of the hydrogenate and of the catalyst in a zone in which the gas-liquid transfer is limited or zero, the said separation and the recycling of the catalyst being carried out in a period of time less than or equal to 30 minutes.

20 Claims, 2 Drawing Sheets

METHOD FOR HYDROGENATING DINITRILES

The present invention relates to a process for the hydrogenation of aliphatic dinitriles at least partly into corresponding aminonitriles.

The hydrogenation of dinitriles into corresponding diamines is a technique which has been known for a long time, in particular the hydrogenation of adiponitrile into hexamethylenediamine, one of the starting materials in the preparation of polyamide 66.

Recent years have seen growing interest in the hydrogenation (also sometimes referred to as hemihydrogenation) of aliphatic dinitriles into aminonitriles, in particular the hydrogenation of adiponitrile into 6-aminocapronitrile, leading, either directly or via caprolactam, to polyamide 6.

Thus, U.S. Pat. No. 5,151,543 describes a process for the selective hydrogenation of aliphatic dinitriles into corresponding aminonitriles, at 25–150° C. and at a pressure greater than atmospheric pressure, in the presence of a solvent in a molar excess of at least 2/1 relative to the dinitrile, the solvent containing liquid ammonia or an alcohol of 1 to 4 carbon atoms containing an inorganic base which is soluble in the said alcohol and in the presence of a Raney catalyst, the aminonitrile obtained being recovered as the main product.

Patent WO-A-93/16034 describes a process for the preparation of 6-aminocapronitrile by hydrogenation of adiponitrile, in the presence of an inorganic base, of a complex of a low-valency transition metal chosen from chromium, tungsten, cobalt, iron and Raney nickel as catalyst, under hydrogen pressure and at a temperature of from 50° C. to 90° C.

Patent WO-A-96/18603 describes the hemihydrogenation of aliphatic dinitriles into aminonitriles, by hydrogen and in the presence of a catalyst based on optionally doped Raney cobalt or nickel and on a strong inorganic base, the initial hydrogenation medium containing water, the aminonitrile and/or the diamine which can be formed and the unconverted dinitrile.

All of these hydrogenation processes lead to the desired aminonitrile and are presented as being able to be carried out continuously in an industrial plant.

However, certain problems have not been revealed for an industrial application. Thus, in the course of research carried out in this field by the Applicant, it has been found that hydrogenation catalysts, and in particular Raney nickel, Raney cobalt, supported metals, in particular the metals from group VIII of the Periodic Table of the Elements, such as nickel, cobalt, ruthenium and rhodium, deposited on a support which is generally an oxide, have a pronounced tendency to become deactivated more rapidly when they are in the presence of nitrile functions and in the absence of hydrogen.

This problem hardly ever arises in the current industrial processes which lead to the diamine, whereas hydrogenation into aminonitrile results in a large amount of nitrile functions being permanently retained in the reaction medium. In such a process, the reaction products, aminonitrile and diamine, need to be recovered, as well as the unconverted dinitrile, while at the same time maintaining or recycling most of the catalyst while it is sufficiently active. Given the above observations, it is thus necessary both to separate the aminonitrile and the diamine formed and the unconverted dinitrile in order to recover them, and to maintain or recycle the catalyst without giving rise to additional deactivation. This therefore involves having operating conditions and apparatus which allow a relatively rapid separation, which is compatible with industrial exploitation, of the catalyst and of the liquid part of the reaction mixture, and also requires the said separation not to result in excessive deactivation of the said catalyst.

A separation, by filtration or centrifugation, of some of the reaction mixture containing the catalyst could be envisaged, but, according to the Applicant's observations, the catalyst thus manipulated in the absence of hydrogen and in the presence of nitrile functions partially loses its activity; the reduction in the lifetime of the catalyst thus weighs unfavourably on the cost-effectiveness of the process. On the other hand, filtration under hydrogen pressure, and thus in the presence of dissolved hydrogen, avoids the deactivation of the catalyst.

The present invention proposes a solution to these various problems. More specifically, it consists of a continuous process for the hydrogenation of dinitrile, at least partly into corresponding aminonitrile, in the presence of a hydrogenation catalyst which is not dissolved in the reaction medium, characterized in that it is carried out in apparatus comprising means for the continuous separation of the hydrogenate and of the catalyst in a zone in which the gas-liquid transfer is limited or zero, the said separation and the recycling of the catalyst being carried out in a period of time less than or equal to 30 minutes.

The apparatus which is suitable for carrying out the process of the invention achieves excellent gas/liquid contact, rapid and effective separation of these two phases after contact, continuous separation of the hydrogenate and of the catalyst and recycling of the latter, in a time which is compatible with the least possible deactivation of the said catalyst.

The said apparatus includes three main sections: a reaction section, a gas-liquid separation section and a catalyst-liquid separation section with recycling of the said catalyst and removal of the liquid (hydrogenate).

The reaction section generally includes one or more U-shaped tubes whose branches are vertical or slightly inclined relative to the vertical, one of the branches of each U allowing for the rise of the gas/liquid/solid catalyst dispersion, the other allowing for the return of the at least partially degassed liquid. It also includes four inlets at the base of the rising branch: the hydrogen inlet, the dinitrile inlet, the inlet for the fresh or regenerated catalyst, with or without co-catalyst, and the recycled catalyst inlet.

The gas-liquid separation section consists of a vertical cylinder including one or more tangential inlets (coming from the rising branch of the reactor), one or more tangential exits (towards the descending branch of the reactor), a gas outlet and an outlet for the reaction mixture towards the liquid-solid separation section. The gas/liquid/solid catalyst dispersion enters at a point below the exit point of the degassed liquid.

The liquid-solid separation section consists of a decanter and/or of a filter which separates the hydrogenate from the catalyst and recycles the said catalyst. The hydrogenate is removed continuously while the catalyst suspension separated out in the decanter and/or in the filter is returned into the reaction section. Flushing is carried out when it is considered necessary to replace some of the catalyst with fresh catalyst.

Figure 1:
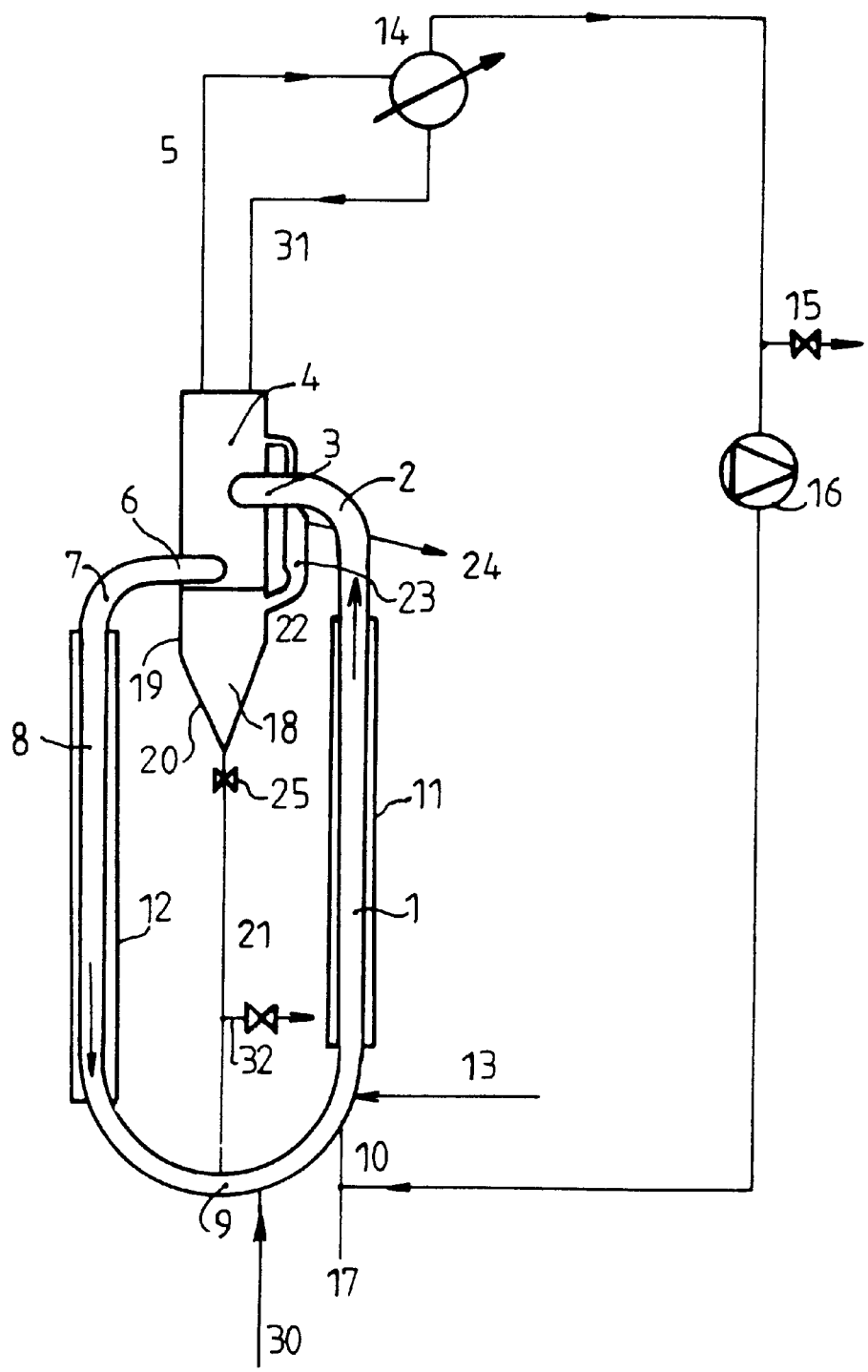
FIG. 1 is a depiction of the apparatus used to carry out the method of the disclosed invention.

The apparatus which is suitable for the process of the invention may be illustrated, for example, by FIG. 1. It includes a cylindrical vertical tube (1) connected, via a bent tube (2), to a horizontal tube (3) emerging tangentially in a gas/liquid separator (4) consisting of a vertical cylinder with a diameter greater than that of the tube (1).

The separator (4) includes pipework (5) for removing gas or vapours. A horizontal tube (6) originating tangentially at the separator and at a point below the inlet point of the tube (3), is connected via a bent tube (7) to a second vertical tube (8) which is connected to the tube (1) via an elbow (9). The tubes (1) and (8) and the elbow (9) together form a U. The tube (1) includes, at its base, pipework (10) for introducing hydrogen and pipework (13) for introducing dinitrile. Tubes (1) and (8) can include, as represented in FIG. 1, a jacket (11) and (12) to allow circulation of a cooling or heating fluid. The elbow (9) includes an inlet (30) for fresh or regenerated catalyst and an inlet (21) for recycled catalyst.

The tubes (1) and (8) can be vertical or slightly oblique (in the latter case, preferably such that their axes converge towards the bottom).

The radii of curvature of the elbows 2, 7 and 9 are calculated according to the usual rules of chemical engineering, such that the loss of charge of the mass circulating in the entire circuit is as low as possible. Their angle of curvature can range from 45° to 135° and preferably from 60° to 120°.

In FIG. 1, hydrogen is introduced via pipework (10). This pipework can be fitted with any common dispersing device, but a simple tube flush with the wall, arranged in the axis of the tube (1) is sufficient. This pipework (10) is connected to a source of hydrogen which can be introduced at atmospheric pressure or at a higher pressure.

The pipework (5) for removing the gases can be connected to any device for processing the gases separated from the hydrogenate. FIG. 1 illustrates a device in which the gases obtained from (5) pass into a condenser (14), in which the vapours conveyed into the separator (4) are separated from the hydrogen. The condensate obtained is recycled into the apparatus via pipework (31). The excess hydrogen then passes into a compressor (16) via a pipe which includes a flushing system (15) and it is then recycled at (10) after introduction at (17) of an amount of hydrogen intended to compensate for the hydrogen consumed during the hydrogenation and for that which has been flushed out.

It is necessary to remove the degassed hydrogenate formed, which has been freed of the catalyst. In order to be able to remove a clear hydrogenate, i.e. one containing virtually no catalyst, a decanter (18) is placed directly under the separator (4). The liquid/catalyst suspension, whose gas phase has been separated out in the separator (4), enters the decanter (18).

The decanter (18) consists of a cylinder (19) ending with a cone (20). A pipe (21) serves to continuously return the concentrated mash of catalyst into the elbow (9). The hydrogenate freed of the catalyst leaves via a pipe (22) connected to a pot (23) fitted with an overspill (24) to allow the clear hydrogenate to be removed continuously, the level in the entire apparatus being kept constant by continuous introduction of an equivalent volume of dinitrile-solvent-catalyst mixture. The flow rate in the tube (21) is adjusted by means of a valve (25) such that the liquid/catalyst mash retains an adequate concentration. The pipework (21) includes pipework (32) for flushing the spent catalyst, which may optionally be regenerated.

Figure 2:
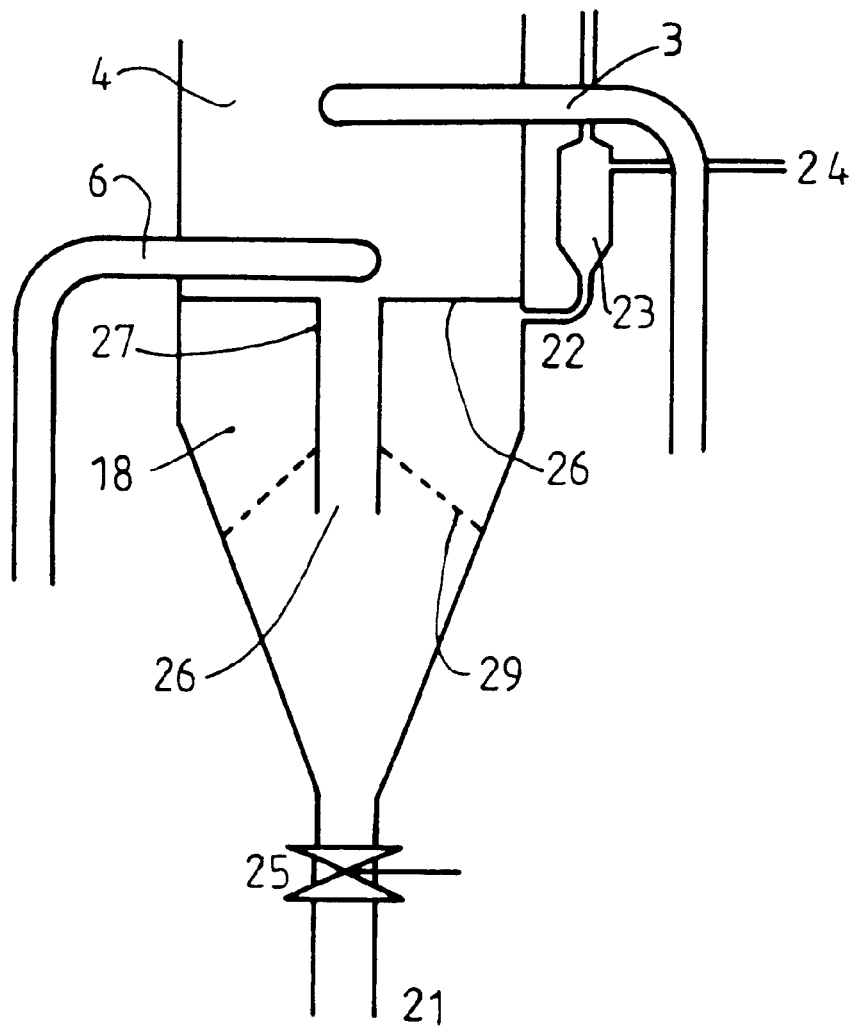
FIG. 2 is a depiction of the decantation method used in the context of the invention.

FIG. 2 illustrates one specific decantation method used in the context of the invention. In order to prevent, on the one hand, excessively rapid movements of the mass of catalyst and of hydrogenate from occurring in the reactor (18) and, on the other hand, hydrogen from penetrating into this decanter, a separation between the two zones (gas-liquid separation section and liquid-solid separation section) is necessary. However, it should not in any way be the cause of a deposition of catalyst. Such a result is obtained by installing a partition (26) between the separator (4) and the decanter (18), circulation between the gas-liquid separator and the decanter being ensured by means of a pipe (27) whose diameter is calculated so as to appreciably reduce the speed of the liquid (for example to a value of less than 0.5 meter/second). This pipe (27) extends inside the decanter via a tube (28) whose diameter is greater than or equal to that of the pipe (27). A large-mesh metal gauze (29), in the shape of an upward-facing cone, can be placed inside the decanter (18) in order to attenuate the turbulences created by the arrival of the liquid/catalyst mash.

The apparatus described above can be modified by adding a filter to the decanter or by replacing the said decanter with a filter.

The use of the apparatus described above in the process for the hemihydrogenation of adiponitrile into 6-aminocapronitrile makes it possible to obtain a good dispersion of the hydrogen in the liquid reaction mixture. This dispersion is stable and homogeneous throughout the U-shaped tube(s). As has been stated above, this apparatus makes it possible to continuously separate, and without any appreciable deactivation of the catalyst, the hydrogenate to be removed from the said catalyst to be recycled. This is possible because the residence time of the catalyst in the decanter (18) and of recycling of the said catalyst can be limited on average to a value of less than or equal to 30 minutes, preferably less than or equal to 15 minutes and even more preferably less than or equal to 5 minutes. These residence times are also respected when the decanter is replaced with a filter or is completed by adding a filter.

In order to obtain good decantation of the catalyst within the time limits indicated above, an average catalyst concentration, corresponding to the catalyst/liquid reaction mixture weight ratio, of greater than 5% will preferably be used. For lower concentrations, some of the catalyst tends to be entrained with the hydrogenate removed, when the maximum residence time in the decanter (18) is respected. In this case, the filtration technique may prove to be advantageous.

An average catalyst concentration of greater than or equal to 10% is again preferred, since it allows even faster decantation of the catalyst, and thus maintenance of the said catalyst under unfavourable conditions for a shorter time, for example less than or equal to 15 minutes.

The aliphatic dinitriles which can be used in the process of the invention are more particularly the dinitriles of general formula (I):

NC—R—CN              (I)

in which R represents a linear or branched alkylene or alkenylene group containing from 1 to 12 carbon atoms.

Dinitriles of formula (I) in which R represents a linear or branched alkylene radical containing from 1 to 6 carbon atoms are preferably used in the process of the invention.

As examples of such dinitriles, mention may be made in particular of adiponitrile, methylglutaronitrile, ethylsuccinonitrile, malononitrile, succinonitrile and glutaronitrile and mixtures thereof, in particular mixtures of adiponitrile and/or of methylglutaronitrile and/or of ethylsuccinonitrile which can be obtained from the same process for the synthesis of adiponitrile.

In practice, the case where $R=(CH_2)_4$ will be the most common since this corresponds to the use of adiponitrile (AdN) in the present process.

The catalyst generally consists of a catalyst based on Raney nickel and/or on Raney cobalt, optionally, but preferably, including one or more doping elements chosen from the elements from groups Ib, IVb, VIb, VIIb and VIII of the Periodic Table of the Elements as published in the Handbook of Chemistry and Physics, 51st Edition (1970–1971).

The catalyst based on Raney nickel and/or on Raney cobalt used in the process can thus include, besides nickel or cobalt and the optional residual amounts of the metal removed from the original alloy when the catalyst is obtained from attack of an alloy, i.e. generally aluminium, one or more other doping elements such as, for example, chromium, titanium, molybdenum, tungsten, iron, zinc or copper.

Among these doping elements, chromium and/or iron and/or titanium are considered the most advantageous. These doping elements usually represent, on a weight basis per weight of nickel or of cobalt, from 0% to 15% and preferably from 0% to 10%.

The catalyst can also consist of a metal, which is generally a metal from group VIII of the Periodic Table of the Elements, such as ruthenium, rhodium, nickel or cobalt, deposited on a support which is generally an oxide such as aluminas, silicas, aluminosilicates, titanium dioxide, zirconium oxide or magnesium oxide.

In the supported metal catalysts, the metal generally represents from 0.1 to 80% of the weight of the support, and preferably from 0.5 to 50%.

Raney nickel, in particular, doped Raney nickel, is preferred in the context of the present invention.

For the composition of the reaction medium, in particular for the nature and amount of solvent and of base, reference may be made more particularly to the description in patent WO-A-96/18603, the content of which is incorporated by way of reference into the present description, or alternatively in patent EP-A-0,641,315.

The examples which follow illustrate the invention.

Tests A AND B

These tests are intended to demonstrate the deactivation of Raney Ni in the presence of nitrile functions and in the absence of hydrogen.

In order for the "normal" consumption of the Ni, due to its catalytic action, not to interfere, only the initial rate of consumption of the hydrogen during the hydrogenation of adiponitrile (AdN) will be taken into account.

66.5 g of AdN, 22.3 g of HMD, 10 g of water, potassium hydroxide in a proportion of 0.4 mol/kg of Ni and 1.2 g of Raney Ni containing 1.8% by weight of Cr are loaded into a reactor.

In Test A which serves as a control, the hydrogenation is carried out immediately at 50° C. and at a hydrogen pressure of 20 bar.

In Test B, the hydrogenation is carried out at 50° C. and at a hydrogen pressure of 20 bar, but before introducing the hydrogen, the reaction mixture is stirred for 30 min under nitrogen at 50° C.

The initial hydrogenation rates measured for these two tests are as follows:

Test A: 24 liters of hydrogen consumed per hour,
Test B: 21 liters of hydrogen consumed per hour.

The maintenance of the catalyst for 30 min in the presence of nitrile functions and in the absence of hydrogen is thus reflected by a 12.5% decrease in the initial activity of the said catalyst.

Test C

In order to distinguish, in Examples 1 to 3 below, the part of "normal" consumption of Raney Ni from that possibly due to the deactivation of the said Raney Ni in the absence of hydrogen, a continuous AdN hydrogenation test was carried out.

The test consists in loading 143.6 g of AdN, 201.1 g of aminocapronitrile (ACN), 134.1 g of hexamethylenediamine (HMD), potassium hydroxide in a proportion of 0.46 mol/kg of Ni and 6.4 g of Raney Ni containing 1.8% by weight of Cr into a reactor stirred by a turbomixer.

After the apparatus has been flushed with hydrogen, the temperature is adjusted to 50° C. and the hydrogen pressure to 25 bar. When the reaction mixture is at the reaction temperature, AdN is injected at a flow rate of 172.5 g/h and aqueous potassium hydroxide solution at 0.02 mol/l is injected at a flow rate of 16.4 g/h.

The reaction mixture is removed continuously by passing it through a filter placed in the reactor. The nickel is not renewed, but the separation is carried out in this test under gas/liquid transfer conditions which provide the catalyst with a constant concentration of hydrogen.

After hydrogenation of 1216 g of AdN, the test is stopped and the activity of the Raney Ni contained in the reactor is measured using the following hydrogenation test.

1 to 2 g of Raney Ni mash are removed, the catalyst is washed with six times 50 ml of distilled water and 0.40 g of catalyst is weighed out accurately in a picnometer. The said catalyst is introduced into a 150 ml stainless-steel autoclave fitted with a stirring system, a heating system, means for introducing hydrogen and reagents and means for measuring the temperature and the pressure. About 0.4 g of water (this amount is taken into account in the weight composition of the 42 g of reaction solvent composed of 90% HMD and 10% water) is also entrained with the catalyst. The HMD, the water and the potassium hydroxide (in a proportion of 0.05% by weight of the reaction mixture) are loaded into the autoclave, under an argon atmosphere. The autoclave is flushed with nitrogen and with hydrogen. It is then heated and is kept at 25 bar of hydrogen (by means of a hydrogen tank). The system for recording the hydrogen pressure in the said tank is switched on and 6 g of AdN are rapidly injected. The hydrogenation is continued until the consumption of hydrogen has ended.

The above test is carried out, on the one hand, with fresh Raney Ni as used in Test C and, on the other hand, with the Raney Ni which was used to carry out Test C (spent Ni). The initial hydrogenation rate measured in this test represents the activity of the Raney Ni. The activity of the spent Ni represents 40% of the activity of the fresh Ni.

The chemical consumption of Ni corresponding to its loss of "normal" activity due to its use as a hydrogenation catalyst is calculated by the product of the amount of Ni loaded (6.4 g) multiplied by the difference in activity before and after Test C (1–0.4), the result being divided by the amount of AdN hydrogenated in the said Test C (1216 g) and is expressed in kg of Ni/t of AdN converted.

This "normal" chemical consumption is 3.15 kg of Ni/t of AdN.

EXAMPLES 1 TO 3

The tests are carried out in apparatus as described in FIGS. 1 and 2.

The hydrogenation is carried out on adiponitrile, the solvent consisting of water (8% by weight relative to the adiponitrile used). The catalyst is a Raney nickel containing 1.8% by weight of chromium dopant relative to the weight of Ni. 15% of catalyst are used relative to the reaction mixture.

The supply rates of the adiponitrile, of the fresh Raney nickel intended to compensate for the "normal" deactivation (wear) of the catalyst, and of the potassium hydroxide solution (aqueous solution at 50% by weight) are indicated in Table 1 below.

The temperature (T° C.) at which each test is carried out, the degree of conversion of the adiponitrile (% DC AdN) the selectivity towards 6-aminocapronitrile relative to the AdN converted (% RY ACN), the selectivity towards hexamethylenediamine relative to the AdN converted (% RY HMD), the chemical consumption of Ni (amount of Ni fully deactivated which has been replaced: Cs of Ni kg/t of AdN converted), the residual activity of the flushed Ni (Act of Ni: as % of the initial activity) are collated in Table 1 below.

For each of the examples, the average residence time of the catalyst in the decanter (18) was 5 minutes.

The hydrogen circulation rate is 9000 Nm³/h and the hydrogen pressure is 25 bar.

TABLE 1

| SUPPLY | | | REACTOR | | | | | |
|---|---|---|---|---|---|---|---|---|
| AdN t/h | Fresh Ni kg/h | KOH at 50% kg/h | T° C. | % DC AdN | % RY ACN | % RY HMD | Cs of Ni kg/t of AdN converted | Act of Ni % |
| 3.66 | 11 | 2.2 | 59 | 88.9 | 25.8 | 73 | 3.1 | 9 |
| 5.0 | 14 | 2.8 | 50 | 70.8 | 42.7 | 55.3 | 3.4 | 14 |
| 6.2 | 15 | 2.1 | 48 | 69.0 | 58.2 | 39.9 | 3.2 | 9 |

The results obtained with the process of the invention show that the chemical consumption of Raney Ni is not higher than in Test C performed while keeping the Ni constantly in the presence of hydrogen. The process of the invention thus allows the continuous hydrogenation of dinitrile into aminonitrile without deactivation of the catalyst other than the normal wear of the said catalyst.

What is claimed is:

1. Process for the continuous hydrogenation of dinitrile to produce at least one corresponding aminonitrile, in the presence of a hydrogenation catalyst which is not dissolved in the reaction medium, comprising, at the hydrogenation reactor outlet, carrying out a separation of the gas contained in the reaction medium, in a zone in which the gas-liquid transfer is limited or zero, reconveying the gas-depleted reaction medium into the said hydrogenation reactor and in removing a portion of said reaction medium from said liquid-gas separation zone after separation of the solid in a liquid-solid separation zone, with recycling of the solid decanted off in the hydrogenation reactor with a residence time of less than 30 minutes of the solid decanted off in said liquid-solid separation zone.

2. Process according to claim 1, wherein the gas-liquid separation is carried out in apparatus formed by a vertical cylinder comprising at least one supply, from the hydrogenation reactor, of the hydrogenation reaction medium, this supply being arranged tangentially on the vertical cylinder, and at least one recycler of the degassed reaction medium into the hydrogenation reactor, this recycler being arranged tangentially on the vertical cylinder at a position below that of said inlet.

3. Process according to claim 1, wherein the liquid-solid separation is carried out by decantation or filtration.

4. Process according to claim 3, wherein the liquid recovered after decantation or filtration is recycled into the liquid-gas separation zone, with purging of the reaction medium containing the hydrogenation products.

5. Process according to claim 1, wherein in that a portion of the catalyst recycled from the solid-liquid separation zone in the hydrogenation reactor is replaced with fresh catalyst.

6. Process according to claim 1, wherein the residence time of the decanted solid in the liquid-solid separation zone is less than 15 minutes.

7. Process according to claim 6, wherein the said residence time is less than 5 minutes.

8. Process according to claim 1, wherein the gas separated in the liquid-gas separation zone is recycled into the hydrogenation reactor.

9. Process according to claim 1, wherein the hydrogenation reactor comprises one or more U-shaped tubes whose branches are vertical or slightly inclined relative to the vertical, one of the branches of each U allowing for the rise of the gas/liquid/solid catalyst dispersion towards the liquid-gas separation zone, the other branch of each U receiving the at least partially degassed liquid medium exiting from the liquid-gas separation zone.

10. Process according to claim 1, wherein the average catalyst concentration, corresponding to the catalyst/liquid reaction mixture weight ratio, is greater than 5% and preferably greater than or equal to 10%.

11. Process according to claim 1 wherein the aliphatic dinitrile comprises dinitriles of general formula (I):

$$NC-R-CN \qquad (I)$$

in which R represents a linear or branched alkylene or alkenylene group containing from 1 to 12 carbon atoms.

12. Process according to claim 1, wherein the aliphatic dinitrile comprises adiponitrile, methylglutaronitrile, ethylsuccinonitrile, malononitrile, succinonitrile and glutaronitrile or mixtures thereof.

13. Process according to claim 1, wherein the aliphatic dinitrile used is adiponitrile.

14. Process according to claim 1, wherein the catalyst used comprising a catalyst based on Raney nickel and/or on Raney cobalt, comprising a doping element comprising elements from groups Ib, IVb, VIb, VIIb or VIII of the Periodic Table of the Elements as published in the Handbook of Chemistry and Physics, 51st Edition (1970–1971).

15. Process according to claim 14, where the catalyst based on Raney nickel and/or on Raney cobalt comprises, besides nickel or cobalt, one or more other doping elements chosen from chromium, titanium, molybdenum, tungsten, iron, zinc and copper.

16. Process according to one of claim 1 wherein the catalyst used comprises a metal from group VIII of the Periodic Table of the Elements deposited on a support which is an oxide.

17. The process according to claim 10, wherein the average catalyst concentration, corresponding to the catalyst/liquid reaction mixture weight ratio, is greater than or equal to 10%.

18. The process according to claim 12, wherein the aliphatic dinitrile comprises mixtures of adiponitrile and/or of methylglutaronitrile and/or of ethylsuccinonitrile which can be obtained from the same process for the synthesis of adiponitrile.

19. The process according to claim 16, wherein the metal comprises ruthenium, rhodium, nickel or cobalt.

20. The process according to claim 16, wherein the support which is an oxide comprises aluminas, silicas, aluminosilicates, titanium dioxide, zirconium oxide or magnesium oxide.

* * * * *